(12) United States Patent
Gutman et al.

(10) Patent No.: US 6,927,300 B2
(45) Date of Patent: Aug. 9, 2005

(54) PROCESS FOR THE PREPARATION OF LATANOPROST

(75) Inventors: Arie Gutman, Haifa (IL); Gennadiy Nisnevich, Haifa (IL); Marina Etinger, Nesher (IL); Igor Zaltzman, Haifa (IL); Lev Judovich, Haifa (IL); Boris Pertsikov, Nesher (IL)

(73) Assignee: FineTech Laboratories LTD, Nesher (IL)

( * ) Notice: Subject to any disclaimer, the term of this patent is extended or adjusted under 35 U.S.C. 154(b) by 0 days.

(21) Appl. No.: 10/181,523

(22) PCT Filed: Jan. 26, 2001

(86) PCT No.: PCT/IL01/00076

§ 371 (c)(1),
(2), (4) Date: Oct. 25, 2002

(87) PCT Pub. No.: WO01/55101

PCT Pub. Date: Aug. 2, 2001

(65) Prior Publication Data

US 2003/0149294 A1 Aug. 7, 2003

(30) Foreign Application Priority Data

Jan. 27, 2000 (IL) .............................................. 134241

(51) Int. Cl.⁷ ............................................. C07C 57/00
(52) U.S. Cl. ...................... 554/222; 554/141; 554/142; 554/159; 554/221; 549/312; 549/466; 549/465
(58) Field of Search ................................ 554/141, 142, 554/159, 221, 222; 549/465, 466, 312

(56) References Cited

U.S. PATENT DOCUMENTS 4,346,228 A * 8/1982 Skuballa et al. ............... 560/53
5,698,733 A 12/1997 Hellberg et al. ............... 560/56
6,689,901 B2 2/2004 Henegar ..................... 562/465

FOREIGN PATENT DOCUMENTS

| EP | 0 850 926 | 7/1998 |
| EP | 0 930 296 | 7/1999 |
| EP | 930296 | * 7/1999 |
| WO | WO 93/00329 | 1/1993 |
| WO | WO 01/87816 | 11/2001 |
| WO | WO 02/096868 | 12/2002 |

OTHER PUBLICATIONS

Resul et al., J. Med. Chem., vol. 36, pp. 243–248, 1993.*
Delong et al., vol. 10, No. 14, pp. 1519–1522, 2000.*
deLong, M.A., et al., "Synthesis and In Vitro Evaluation of Human FP–receptor Selective Prostaglandin Analogues," *Bioorg. Med. Chem. Lett.* 10:1519–1522, Elsevier Science Ltd. (Jul. 2000).
Disselnkötter, H., et al., "Synthese von Prostaglandin–Analoga," *Liebigs Ann. Chem.*, 150–166, Verlag Chemie GmbH (1982).
Dolence, E.K., et al., "Utilization of a Nitrenium Ion Cyclization in a Synthesis of a Photoactive Prostaglandin, 17–(4–Azido–2–Hydroxyphenyl)–18,19,20–Trinorprostaglandin $F_{2\alpha}$," *Tetrahedron Lett.* 28:43–46, Pergamon Journals Ltd. (1987).
Resul, B., et al., "Phenyl–Substituted Prostaglandins: Potent and Selective Antiglaucoma Agents," *J. Med. Chem.* 36:243–248, American Chemical Society (1993).
Database CAPLUS, Accession No. 1992:511373, English language abstract for Japanese Patent Publication No. 4–74162 (Document AM1), American Chemical Society (1992).
International Search Report for International Patent Application No. PCT/IL01/00076, mailed Dec. 21, 2001.

* cited by examiner

*Primary Examiner*—Deborah D. Carr
(74) *Attorney, Agent, or Firm*—Pearl Cohen Zedek Latzer, LLP; Mark Cohen

(57) ABSTRACT

Disclosed is a process for the preparation of the antiglaucoma drug Latanoprost, in good yield, in large amounts and with desired purity. Also disclosed are novel intermediates for the above process.

15 Claims, No Drawings

PROCESS FOR THE PREPARATION OF LATANOPROST

CROSS-REFERENCE TO RELATED APPLICATIONS

This application is a National Phase Application of PCT International Application No. PCT/IL01/00076, International Filing Date Jan. 26, 2001, claiming priority of Israeli Patent Applications, IL 134241, filed Jan. 27, 2000.

FIELD OF THE INVENTION

This invention relates to a novel process for the preparation of 13,14-dihydro-17-phenyl-18,19,20-trinor-PGF$_{2\alpha}$ isopropyl ester (Latanoprost) of the formula [1]:

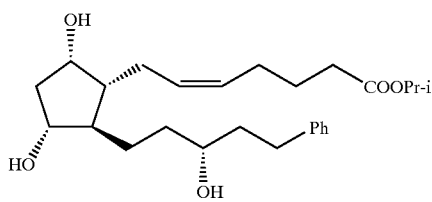

[1]

drug for treating glaucoma (Merck Index, 12th Ed., 5787).

BACKGROUND OF THE INVENTION

The known methods for synthesis of Latanoprost (see B. Resul et al., J. Med. Chem., 1993, 36, 243) include the stage of reducing of lactone-group of the compound [20] with excess of diisobutylaluminum hydride (DIBAL-H) at −72−−80° C. to give the compound [11b] (Scheme 1):

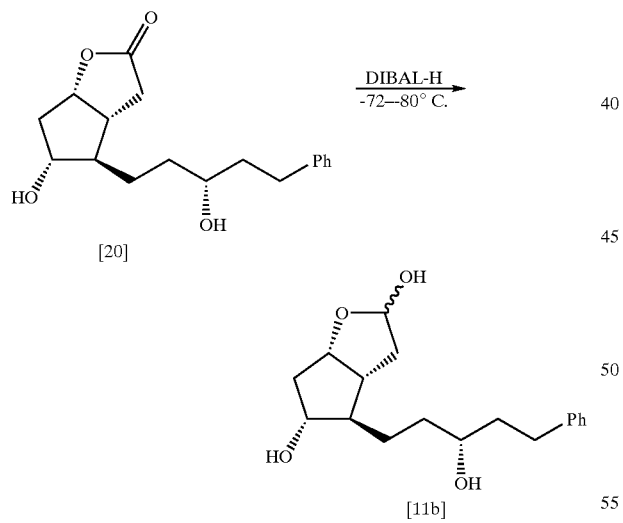

However, this method is problematic as it is difficult to scale-up this highly exothermic reaction at such low temperature conditions. Furthermore, it was feared that increasing of temperature during DIBAL-H addition may lead to undesired processes in reduction of product [11b].

OBJECTS OF THE INVENTION

It is an object of this invention to provide a novel process for the preparation of Latanoprost in good yield, in large amounts and with desired purity.

It is a further object of this invention to provide novel intermediates for the above process.

SUMMARY OF THE INVENTION

The above objects are achieved by present invention, which provides a process for the preparation of Latanoprost [1]

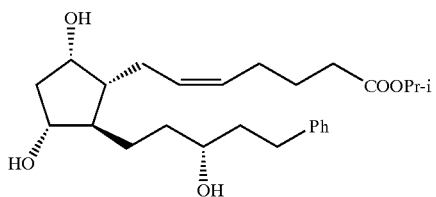

[1]

which comprises deriving the compound [5]

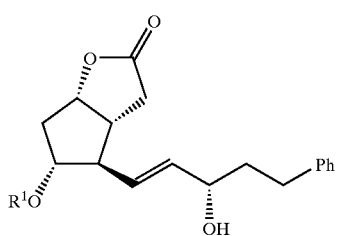

[5]

to give the compound [7]

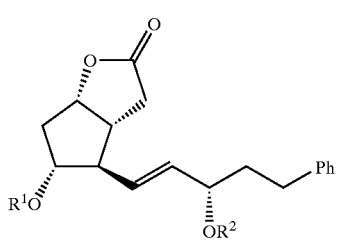

[7]

which is hydrogenated in the presence of catalyst to give the compound of the Formula [9]

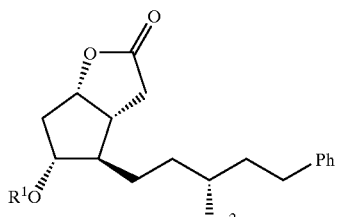

[9]

which is reduced with diisobutylaluminum hydride at temperature range from −50 to +50° C. followed by hydrolysis of the obtained reaction mixture under basic conditions to give compound [11], which is converted into latanoprost [1]

[11]

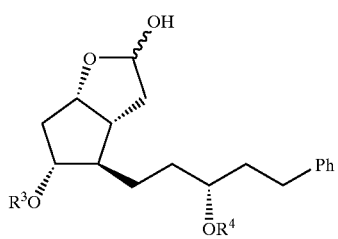

werein one of R¹ and R² is an aryl carbonyl and the other one is selected from the group consisting of aryl carbonyl, acyl, trialkylsilyl, dialkylarylsilyl, 1-alkoxyalkyl, unsubstituted and alkyl-substituted tetrahydro-2H-pyran-2-yl and tetrahydrofuran-2-yl groups;

R³ is hydrogen when R¹ is acyl and is equal to R¹ when it is trialkylsilyl, dialkylarylsilyl, 1-alkoxyalkyl, unsubstituted or alkyl-substituted tetrahydro-2H-pyran-2-yl or tetrahydrofuran-2-yl groups; and R⁴ is hydrogen when R² is acyl and is equal to R² when it is trialkylsilyl, dialkylarylsilyl, 1-alkoxyalkyl, unsubstituted or alkyl-substituted tetrahydro-2H-pyran-2-yl or tetrahydrofuran-2-yl groups.

Some of the new compounds [7] and [9] which are obtained as intermediates in the process of the present invention may be purified by crystallization from organic solvents. This fact represent a further aspect of the invention.

DETAILED DESCRIPTION OF THE INVENTION

An advantage of the present invention is the fact that the highly selective reduction of lactone-group of the compound [9] with diisobutylaluminum hydride may proceed at industrially acceptable temperature range from −50 to +50° C., preferably from −20 to +20° C. On the basis of this we developed a new effective process for synthesis of Latanoprost [1] which process comprises the steps of:

a) stereoselective reduction of oxo-group of compound of the Formula [4]:

[4]

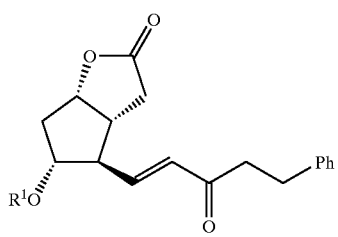

wherein R¹ is defined as above, to yield a mixture of compounds of the Formula [5] (main product) and [6] (minor product):

[5]

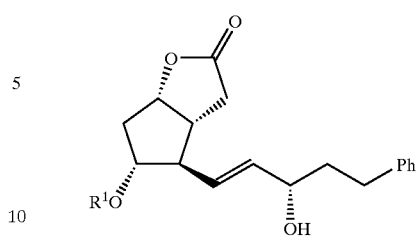

[6]

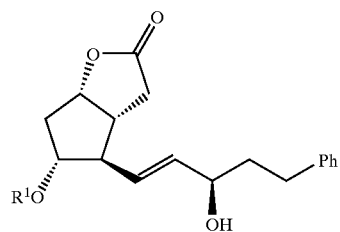

wherein R¹ is defined as above;

b) separating the desired compound [5] from the by-product [6] by column chromatography followed by oxidation of the hydroxy-group of the compound [6] for regeneration of compound [4].

c) deriving compound [5] to give compound [7]:

[7]

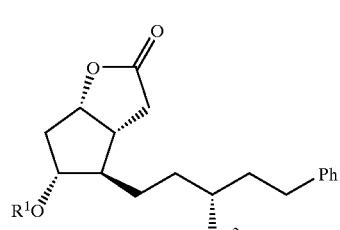

wherein R¹ and R² are as defined above;

d) hydrogenating compound [7] in the presence of a catalyst to yield compound [9]:

[9]

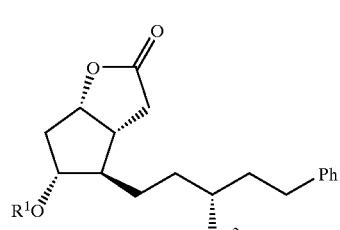

wherein R¹ and R² are as defined above;

e) reducing compound [9] with diisobutylaluminum hydride at temperature −50 to +50° C. followed by hydrolysis of the obtained reaction mixture under basic conditions to give compound [11]:

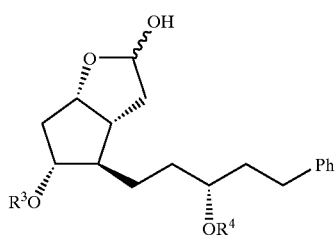

[11]

wherein R³ and R⁴ are as defined above;

f) reacting compound [11] with metal salt of 5-(triphenylphosphoranylidene)pentanoic acid to obtain compound [13]:

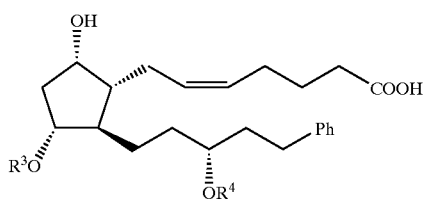

[13]

wherein R³ and R⁴ are as defined above;

g) esterifying compound [13] with compound [16]:

$$(CH_3)_2CHX \qquad [16]$$

wherein X is a leaving group, in the presence of base to obtain the compound of the Formula [17]:

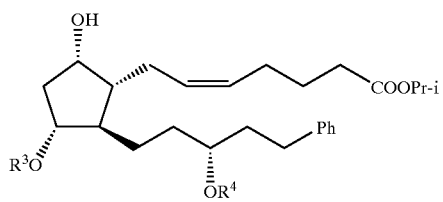

[17]

wherein R³ and R⁴ are as defined above; and, h) when one of R³ or R⁴ in compound [17] is other than hydrogen removing the protecting group to yield Latanoprost [1].

The described process of Latanoprost [1] production may be summarized by the following Scheme 2.

Scheme 2

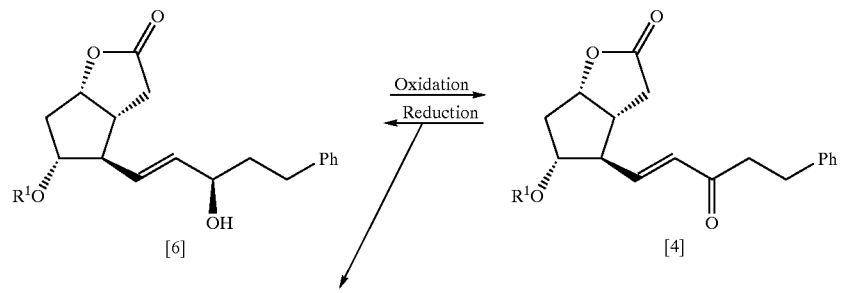

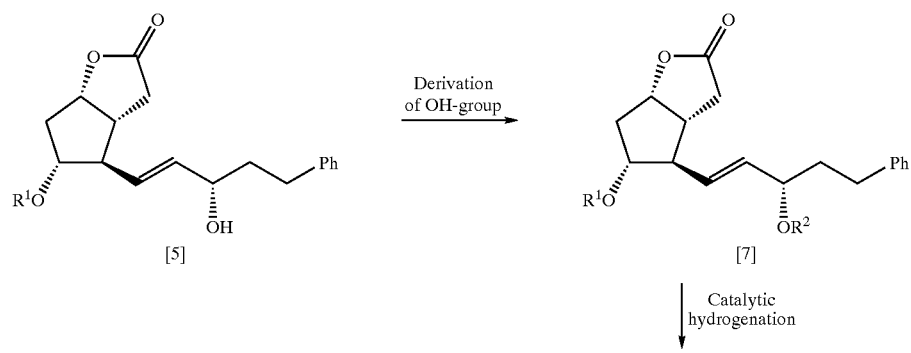

-continued
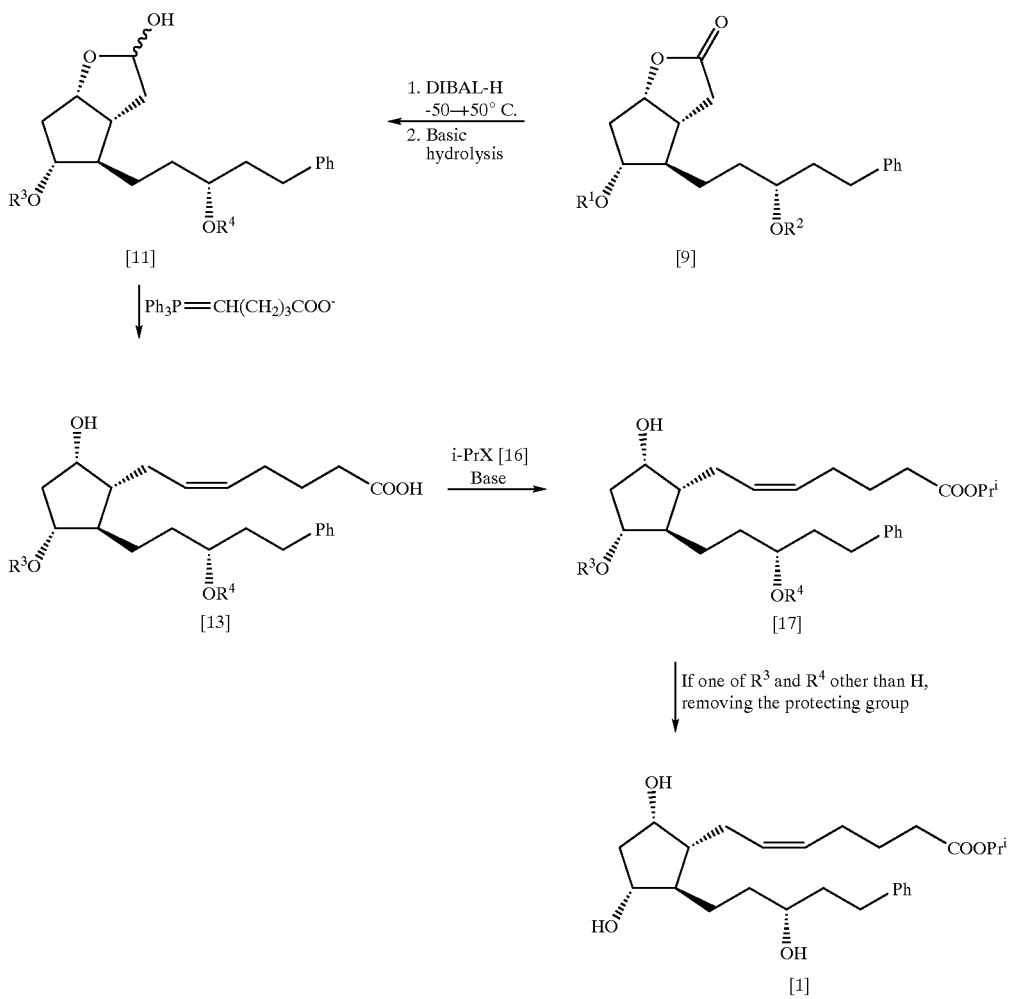
wherein $R^1$, $R^2$, $R^3$, $R^4$ and X are as defined above.
If one of $R^3$ or $R^4$ is other than hydrogen, Latanoprost [1] may alternatively be prepared from the compound [11] through Latanoprost acid [13b] according to Scheme 3:
Scheme 3
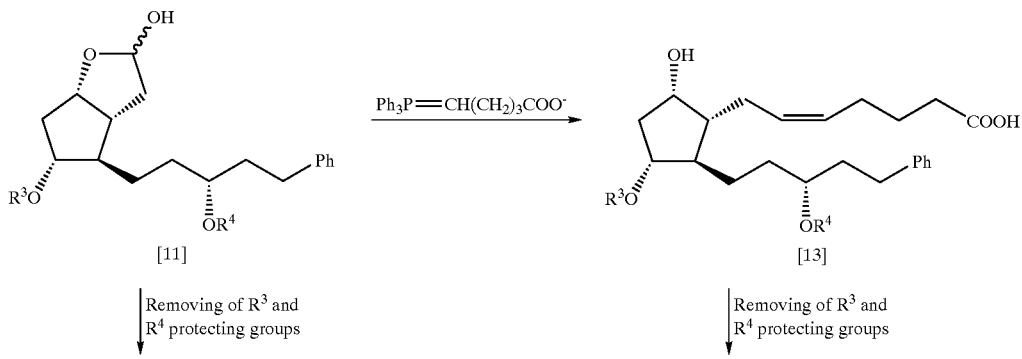

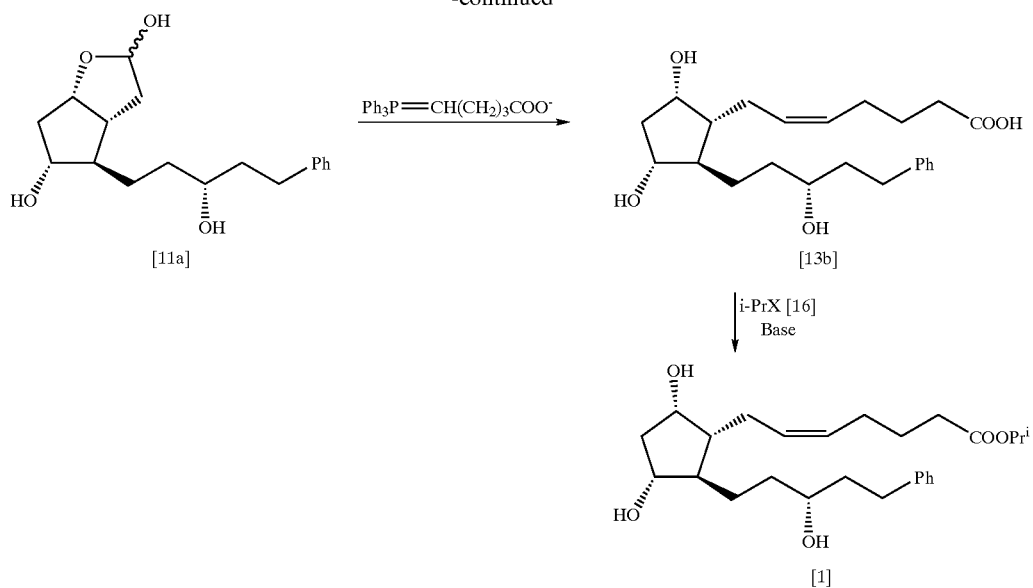

wherein $R^3$, $R^4$ and X are as defined above and one of $R^3$ or $R^4$ other than hydrogen.

Alternatively, compound [9] may be prepared reducing of compound [5] followed by deriving obtained compound [21] to give compound [9] (Scheme 4):

An alternative approach to prepare compound [7] may involve deriving the mixture of the compounds [5] and [6], formed after reducing of the ketone [4], to give a mixture of the compounds [7] and [8], separating the compound [7] from the by-product [8] by column chromatography and/or fractional crystallization, removing $R^2$-protecting group from the compound [8] to give the compound [6] following oxidizing the hydroxy-group of the compound [6] for regeneration of the compound [4] (Scheme 5):

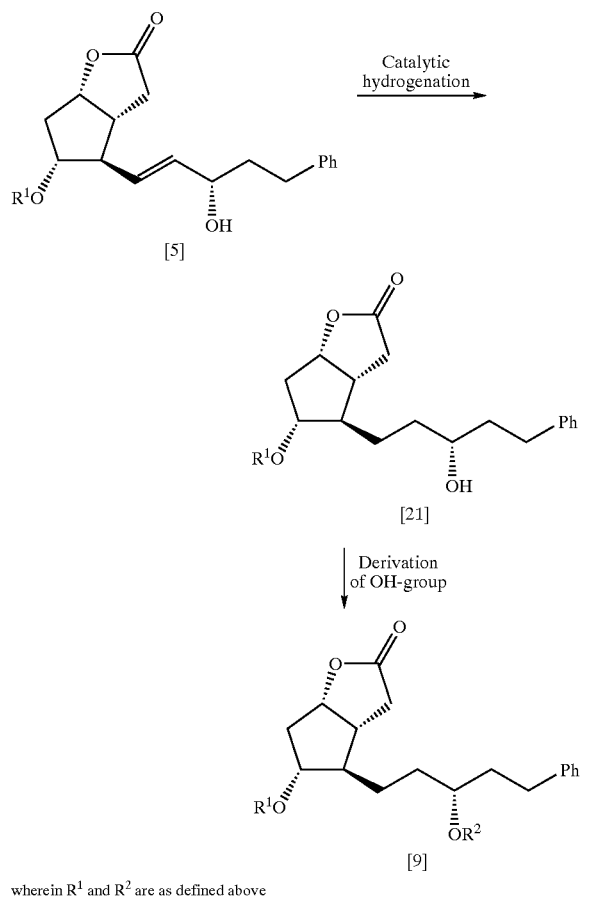

wherein $R^1$ and $R^2$ are as defined above

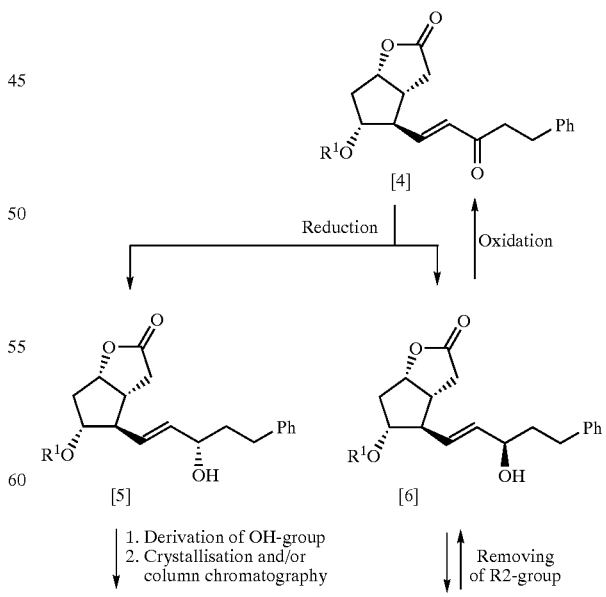

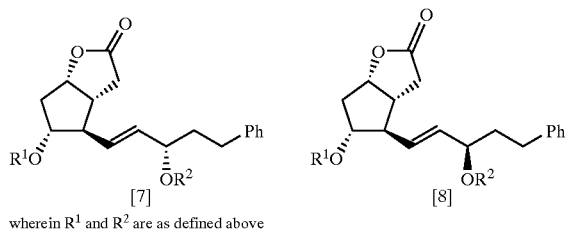

wherein R¹ and R² are as defined above

Preferably the R¹ and R² are selected from the group consisting of benzoyl, p-toluoyl, p-phenylbenzoyl and tetrahydro-2H-pyran-2-yl groups.

Preferably the stereoselective reduction of the compound [4] is carried out with (−)-B-chlorodiisopinocamphenylborane or with borane in the presence of 2-alkyl-CBS-oxazaborolydines. More preferably the said reduction is carried out with (−)-B-chlorodiisopinocamphenylborane in organic solvent. Preferably the said organic solvent is tetrahydrofuran, ether, 1,2-dimethoxyethane, toluene, hexane, dichloromethane or mixture thereof.

Preferably the catalyst for hydrogenation of compound [7] to compound [9] must contain palladium, platinum or nickel. More preferably the catalyst is palladium-on-carbon, platinum oxide or platinum-on-carbon. Preferably the said hydrogenation is provided in the presence of solvents and bases or salts. Preferably the said bases are selected from the group consisting tertiary and secondary amines. Preferably the said salts are selected from the group consisting of metal nitrites, metal alkanoates and metal benzoates.

It is important in the process of the present invention that some new compounds [7] and [9] may be purified by crystallization from organic solvents.

If reduction of compound [9] is carried out with not more than 2 equivalents of diisobutylaluminum hydride (DIBAL-H), intermediate [10] may be isolated from the reaction mixture. Basic hydrolysis of the compound [10] gives the compound [11]. It should be noted that using excess of diisobutylaluminum hydride (DIBAL-H) for reduction of compound [9] to compound [11] at −50–+50° C. is complicated by further reduction to by-product [12]:

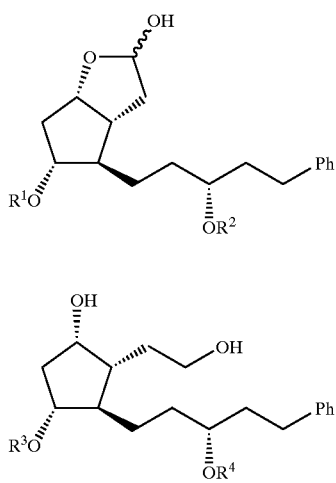

wherein R¹, R², R³ and R⁴ are as defined above.

To increase the yield of [11] it is desirable to add DIBAL-H to compound [9] at −50–+50° C. (preferably at −20–+20° C.) to reach not more than 93–99% conversion of lactone-groups. Preferably, this reaction is conducted in the presence of an organic solvent. Preferably, the organic solvent is toluene, tetrahydrofuran, ether, dichloromethane or mixture thereof. Preferably, the following basic hydrolysis is conducted with organic bases or metal hydroxides or carbonates in a solvent possibly in the presence of phase transfer catalyst. Preferably the metal is alkali or alkaline-earth metal and the solvent is a neutral organic solvent, $C_{1-4}$ alkanol or water or mixture thereof. Process of reduction of the compound [9] with diisobutylaluminum hydride may be presented by Scheme 6:

Scheme 6

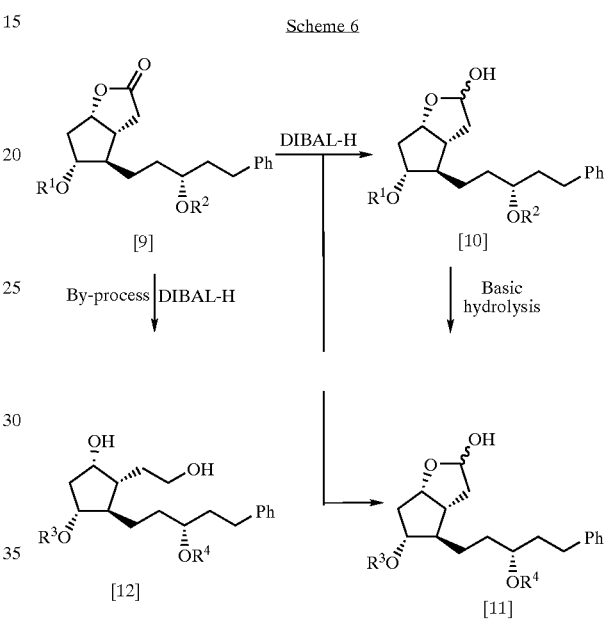

wherein R¹, R², R³ and R⁴ are as defined above

It is desired to purify the compound [13] by column chromatography or/and crystallization its salt with amine from a solvent following isolation of purified compound [13] from the salt. Preferably the said amine is tromethamine, histamine, L-arginine, triptamine or adamantanamine.

Preferably the esterifying of the compound [13] is provided with isopropyl iodide, bromide, methanesulfonate, p-toluenesulfonate, p-nitrophenylsulfonate, 2,4-dinitrophenylsulfonate or triflate in the presence of organic solvent and organic or inorganic base. Preferably the said organic base is 1,8-diazabicyclo[5.4.0]undec-7-ene (DBU), N,N-diisopropylethylamine or diisopropylamine. Preferably the said inorganic base is alkali or alkaline-earth metal carbonate or hydroxide. Most preferably, the said inorganic base is potassium or cesium carbonate. Preferably the said solvent is acetone, methyl ethyl ketone, THF, DMF, dichloromethane, ethanol, isopropanol or acetonitrile.

The compound [4] may be prepared from the commercially available compounds [2a–c] according to Scheme 7:

Scheme 7

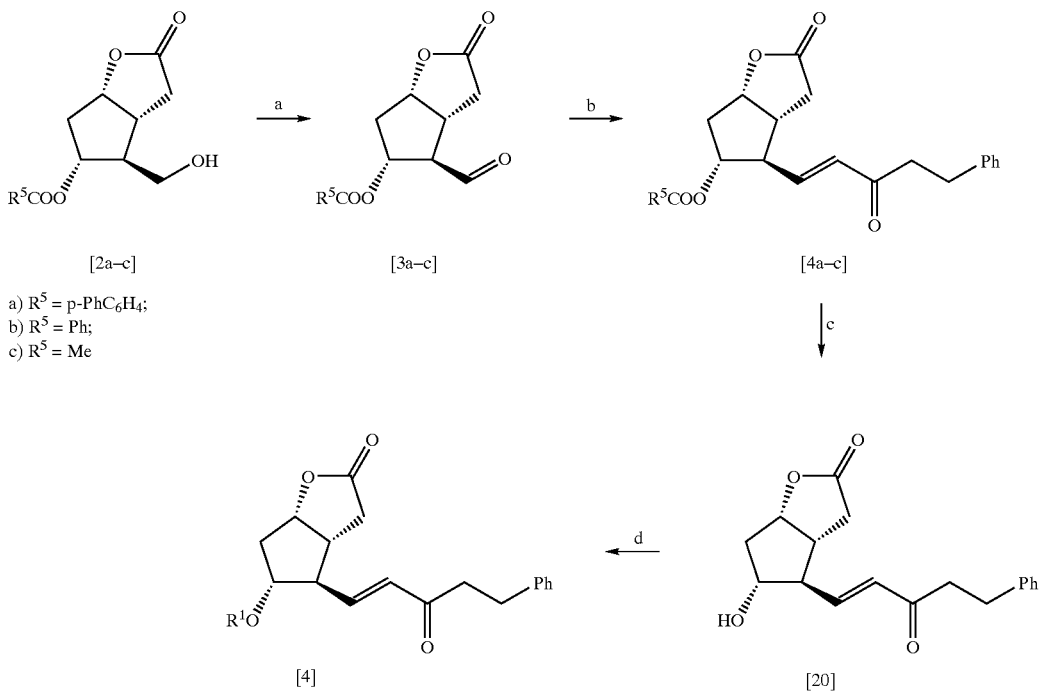

[2a–c]    [3a–c]    [4a–c]

a) $R^5$ = p-PhC$_6$H$_4$;
b) $R^5$ = Ph;
c) $R^5$ = Me

[4]    [20]

wherein $R^1$ is as defined above
Reagents:
(a) Dess-Martin reagent;
(b) PhCH$_2$CH$_2$COCH$_2$PO(OMe)$_2$ and Base or PhCH$_2$CH$_2$COCH=PPh$_3$;
(c) Basic hydrolysis; (d) Derivation of OH-group.

This invention will be better understood from the Examples that follows. However, the examples illustrate, but do not limit, the invention. Those skilled in the art will readily appreciate that the specific methods and results discussed are merely illustrative of the invention as described more fully in the claims that follow thereafter.

EXAMPLE 1

(3aR,4R,5R,6aS)-Hexahydro-4-(3-oxo-5-phenyl-1E-pentenyl)-5-(p-phenylbenzoyloxy)-2H-cyclopenta[b]furan-2-one [4a]

Scheme 8

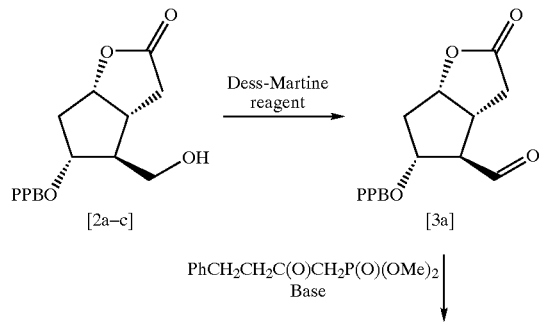

[2a–c]    [3a]

PhCH$_2$CH$_2$C(O)CH$_2$P(O)(OMe)$_2$
Base

-continued

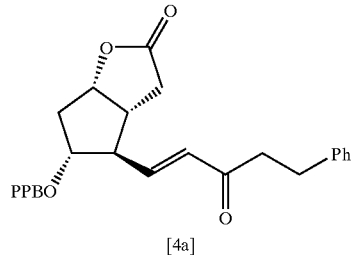

[4a]

wherein PPB is p-phenylbenzoyl group.

1) Preparation of dimethyl (2-oxo-4-phenylbutyl) phosphonate
1.1) 1-Bromo-4-phenyl-2-butanone A freshly prepared solution of bromine (258.9 g) in methanol (600 mL) was added dropwise during 1 h 20 min to a stirred solution of benzylacetone (222.3 g) in methanol (600 mL) at 7–10° C. An exothermic reaction took place, and to maintain the necessary temperature (7–10° C.), the flask should be immersed in a ice-water bath. When orange-red color of bromine disappeared, water (1500 mL) was added to the mixture and the obtained mixture was stirred overnight. The organic layer (on the bottom) was separated, water phase was extracted with dichloromethane (2×600 mL). The combined organic layers were dried over sodium sulfate, filtered and evaporated under reduced pressure. The oily residue was dissolved in hexane (2500 mL) and the obtained solution was kept overnight at −10° C. Precipitated fine crystals (needles) were filtered off, washed on filter with cold hexane, dried under reduced pressure at room temperature to give 1-bromo-4-phenyl-2-butanone (213.0 g, 63% yield), mp 39–40° C. $^1$H NMR (CDCl$_3$) δ 2.95–3.00 (m, 4H); 3.83 (s, 2H); 7.16–7.30 (m, 5H).

1.2) 1-Iodo-4-phenyl-2-butanone

A solution of 1-bromo-4-phenyl-2-butanone (18.9 g) in dry acetone (100 mL) was added dropwise to a stirred solution of sodium iodide (14.0 g) in dry acetone (100 mL) at room temperature. A precipitate of sodium bromide immediately formed. The mixture was stirred overnight at room temperature, filtered and evaporated under reduced pressure. The residue was dissolved in dichloromethane (150 mL). The solution was washed with water, dried over sodium sulfate and evaporated under reduced pressure. The oily residue was dissolved in 95% ethanol (100 mL). The obtained solution was kept at –10° C. overnight. Precipitated pale yellow needles were filtered off, dried under reduced pressure at room temperature to obtain 20.0 g (88% yield) of 1-iodo-4-phenyl-2-butanone, mp 44–45° C. $^1$H NMR (CDCl$_3$) δ: 2.88–3.07 (m, 4H); 3.75 (s, 2H); 7.16–7.31 (m, 5H).

1.3) Dimethyl(2-oxo-4-phenylbutyl)phosphonate

A 0.5 L four necked flask equipped with condenser connected to bubbler, thermometer, dropping funnel with pressure equalization arm and deep-tube for bubbling argon through the reaction mixture was charged with a solution of 1-iodo-4-phenyl-2-butanone (89.5 g) in acetonitrile (250 mL). Trimethylphosphite (80.9 g) was added dropwise to the solution, over 1.5 h, with simultaneous bubbling of an argon through the reaction mixture. The temperature of the reaction mixture was allowed to change from 23° C. to 43° C. The resulting mixture was refluxed during 1 h and evaporated under reduced pressure. The residue was fractionally distilled at 0.05 mm Hg to give 71.0 g (85% yield) of dimethyl (2-oxo-4-phenylbutyl)phosphonate, bp 129–130° C./0.05 mm Hg. $^1$H NMR (CDCl$_3$, δ) 2.88–2.92 (m, 4H); 2.98 (t, J=23 Hz; 2H); 3.68 (s, 3H); 3.74 (s, 3H); 7.14–7.24 (m, 5H).

2) Preparation of (3aR,4R,5R,6aS)-4-formylhexahydro-5-(p-phenylbenzoyloxy)-2H-cyclopenta[b]furan-2-one [3a]

Corey lactone [2a] (80.7 g) was added by portions to a stirred suspension of Dess-Martine reagent (116.6 g) in dichloromethane (700 mL) at 0–3° C. (ice/water bath). The mixture was stirred for 40 min (temperature rose to 14° C.) until lactone [2a] spot disappeared in TLC monitoring. The resulting mixture poured into a solution of sodium bicarbonate (130 g) and sodium thiosulfate pentahydrate (350 g) in water (1.5 L). The mixture was stirred for about 10 min. The organic layer was separated and the water layer was extracted with dichloromethane (2×350 mL). The combined organic solutions were washed with saturated solution of sodium bicarbonate, dried over sodium sulfate, filtered and immediately introduced into the following step.

3) Preparation of (3aR,4R,5R,6aS)-hexahydro-4-(3-oxo-5-phenyl-1E-pentenyl)-5-(p-phenylbenzoyloxy)-2H-cyclopenta[b]furan-2-one [4a]

A solution of dimethyl (2-oxo-4-phenylbutyl) phosphonate (69.1 g) in dichloromethane (200 mL) was added dropwise at 0° C. to a suspension of sodium hydride (11.9 g) in dichloromethane (700 mL). The mixture was stirred at 0° C. during 1 h. The cold (0–5° C.) solution of aldehyde [3a] in dichloromethane prepared in the previous stage was added dropwise to the stirred mixture at 0–5° C. The obtained mixture was stirred for 1 hour at the same temperature (TLC monitoring), filtered through Celite and acidified with acetic acid to pH 5 at 0–5° C. The organic layer was separated, washed with water until the pH of the water layer was not less than 6.8, dried over sodium sulfate, filtered and evaporated under reduced pressure. The oily residue was triturated with ether (500 mL). The precipitated crystals were filtered and dried under reduced pressure to a constant weight to give 93.4 g (85% yield) of crude crystalline product. A solution of the product in acetonitrile was passed through Celite and evaporated under reduced pressure The crystalline residue was recrystallizated from methanol (2 L) gave 83.6 g (76.2% yield) of compound [4a] with mp 134–135° C. and $[\alpha]_D^{20}$ –141.7° (c 1.26, MeCN). $^1$H NMR (CDCl$_3$, δ) 2.32–2.63 (m, 3H); 2.84–2.97 (m, 7H); 5.00–5.10 (m, 1H); 5.20–5.35 (m, 1H); 6.20 (d, J=16 Hz, 1H); 6.65 (dd, J=16 and 8 Hz, 1H); 7.15–7.67 (m, 12H); 8.03 (d, J=8 Hz, 2H).

EXAMPLE 2

(3aR,4R,5R,6aS)-Hexahydro-5-(p-phenylbenzoyloxy)-4-[(3S)-5-phenyl-3-[(tetrahydro-2H-pyran-2-yl)oxy]-1E-pentenyl]-2H-cyclopenta[b]furan-2-one [7a]

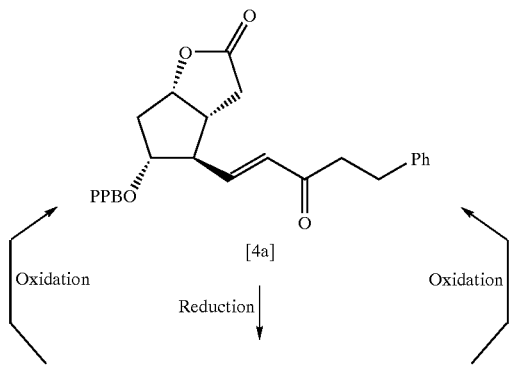

Scheme 9

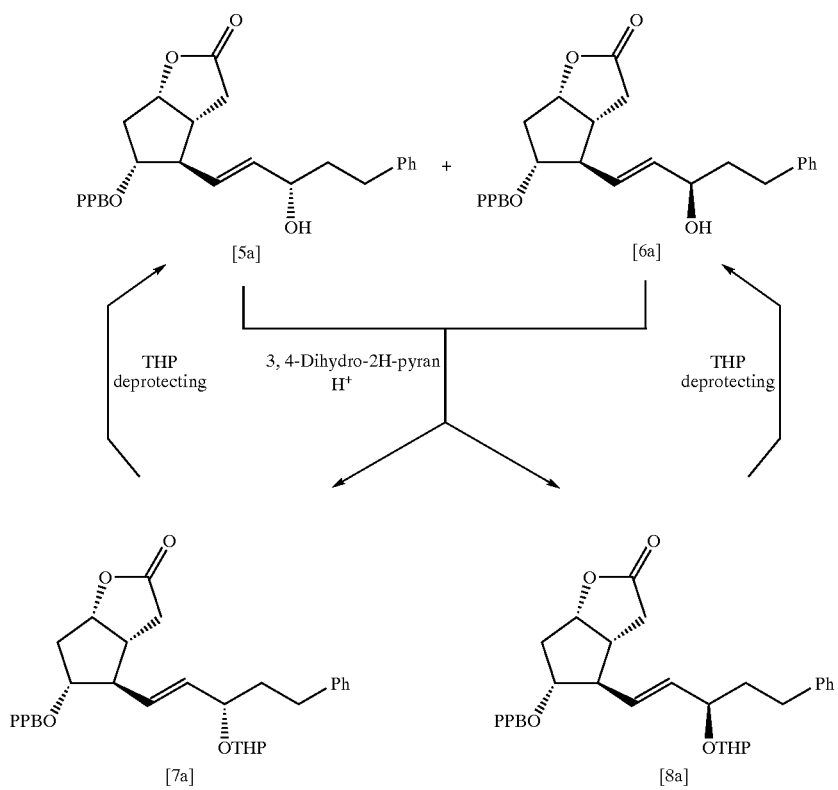

1) Preparation of (3aR,4R,5R,6aS)-hexahydro-4-[(3S) and (3R)-3-hydroxy-5-phenyl-1E-pentenyl]-5-(p-phenylbenzoyloxy)-2H-cyclopenta[b]furan-2-ones [5a] and [6a]

A solution of (−)-B-chlorodiisopinocamphenylborane (26.0 g) in THF (150 mL) was added dropwise at −23—−25° C. to a stirred solution of the compound [4a] (26.0 g) in THF (250 mL). The mixture was stirred at this temperature during 8 h (TLC monitoring) and then quenched by adding 30 mL of Methanol at −23—−25° C. The resulting solution was allowed to warm to room temperature and was stirred at this temperature for 14 h. The mixture was concentrated to a volume 70–100 mL and dichloromethane (400 mL) and water (200 mL) were added to it. The organic layer was separated, water layer was extracted with dichloromethane (3×100 mL). The combined organic layers were washed with a 25 wt. % aq. solution of ammonium chloride (2×80 g), dried over sodium sulfate, filtered and evaporated under reduced pressure. The residue ([5a]/[6a] 95:5 by HPLC) was triturated with hexane (150 mL) and the obtained solid was filtered off. This solid with methanol (20 mL) and isopropyl ether (130 mL) was refluxed during 30 min and cooled to room temperature. The precipitated solid was filtered off and dried under reduced pressure to give 22.0 g (85% yield) of a mixture of compounds [5a] and [6a], where [5a]/[6a] is 96:4 by HPLC.

2) Preparation of (3aR,4R,5R,6aS)-hexahydro-5-(p-phenylbenzoyloxy)-4-[(3S)-5-phenyl-3-[(tetrahydro-2H-pyran-2-yl)oxy]-1E-pentenyl]-2H-cyclopenta[b]furan-2-one [7a] and its (3R)-isomer [8a]

Pyridinium p-toluenesulfonate (0.2 g) was added to a stirred solution of diastereomeric alcohols [5a] and [6a] (23.8 g, [5a]/[6a] 96:4 by HPLC), and 3,4-Dihydro-2H-pyran (15.7 g) in dichloromethane (250 mL) at room temperature. The mixture was stirred overnight at room temperature (TLC monitoring), washed with saturated aqueous solution of sodium bicarbonate and brine, dried over sodium sulfate, filtered and evaporated under reduced pressure. The residue was crystallized from methanol to give 19.9 g (71.1% yield) the compound [7a]. Analytical probe of the compound [7a] may be prepared by repeated crystallization from mixture of hexane and ethyl acetate gave the compound [7a] with mp 118–119° C. and $[\alpha]_D^{20}$ −91.2° (c 1, MeCN). $^1$H NMR (CDCl$_3$) δ: 7.96 (d, J=8 Hz, 2H); 7.50–7.56 (m, 4H); 7.29–7.40 (m, 3H); 7.01–7.17 (m, 5H); 5.38–5.61 (m, 2H); 5.15–5.18 (m, 1H); 4.95–5.00 (m, 1H); 4.42–4.53 (m, 1H); 3.95–4.05 (m, 1H); 3.55–3.80 (m, 1H); 3.15–3.40 (m, 1H). $^{13}$C (CDCl$_3$) δ: 19.4; 19.6; 25.3; 25.4; 30.7; 30.8; 31.2; 31.8; 34.5; 34.8; 36.3; 37.2; 37.4; 37.6; 42.4; 42.5; 53.8; 62.3; 62.4; 74.8; 78.6; 79.0; 82.8; 83.2; 94.9; 98.0; 125.7; 127.0; 127.1; 128.0; 128.1; 128.2; 128.6; 128.8; 130.0; 131.3; 133.7; 134.6; 139.8; 141.7; 145.9; 146.0; 165.7; 176.0; 176.2. IR (KBr): 2933; 1762; 1716; 1670; 1640; 1268 cm$^{-1}$.

The mother liquor which contains a mixture of the compounds [7a] and [8a] was evaporated under reduced pressure and subjected separation by column chromatography on Silica gel (elution with ethyl acetate/hexane 1:2 v/v) to afford additional 2.0 g (8.4%) of compound [7a] and 0.9 g (3.8%) of isomer [8a] with mp 116–118° C. and $[\alpha]_D^{20}$ −84.3° (c 1, MeCN). $^1$H NMR (CDCl$_3$) δ: 7.06–8.04 (m, 14H); 5.40–5.67 (m, 2H); 5.22–5.39 (m, 1H); 5.00–5.15 (m, 1H); 4.61 (m, 1H); 4.02–4.17 (m, 1H); 3.78–3.87 (m, 1H);

3.30–3.50 (m, 1H); 2.45–2.93 (m, 7H); 2.18–2.28 (m, 1H); 1.53–2.03 (m, 8H).

3) Preparation of (3aR,4R,5R,6aS)-hexahydro-4-[(3R)-3-hydroxy-5-phenyl-1E-pentenyl]-5-(p-phenylbenzoyloxy)-2H-cyclopenta[b]furan-2-one [6a]

Pyridinium p-toluenesulfonate (20 mg) was added to a stirred solution of the compound [8a] (0.44 g), obtained in previous step, in methanol (20 mL) at room temperature. The mixture was stirred at 40–50° C. for 3–4 hours (TLC monitoring) and evaporated under reduced pressure. The residue was diluted with dichloromethane (30 mL). The solution was washed with saturated aqueous solution of sodium bicarbonate (10 mL) and brine(10 mL), dried over sodium sulfate, filtered and evaporated to give 0.35 g (93.4%) of oily residue. The residue was crystallized from a mixture of hexane and ether to give compound [6a] as white crystals with mp 81–83° C. and $[\alpha]_D^{20}$ –124.5° (c 1, MeCN). $^1$H NMR (CDCl$_3$) δ: 7.08–8.05 (m, 14H); 5.51–5.74 (m, 2H); 5.21–5.30 (m, 1H); 5.02–5.07 (m, 1H); 4.09–4.13 (m, 1H); 2.46–2.92 (m, 7H); 2.18–2.28 (m, 1H); 1.66–1.86 (m, 3H). $^{13}$C (CDCl$_3$) δ: 31.6; 34.8; 37.6; 38.7; 42.7; 54.1; 71.6; 79.0; 83.1; 125.9; 127.1; 127.2; 128.2; 128.3; 128.8; 128.9; 130.1; 136.2; 139.9; 141.5; 146.1; 165.9; 176.2.

4) Preparation of (3aR,4R,5R,6aS)-hexahydro-4-[(3S)-3-hydroxy-5-phenyl-1E-pentenyl]-5-(p-phenylbenzoyloxy)-2H-cyclopenta[b]furan-2-one [5a]

Pyridinium p-toluenesulfonate (50 mg) was added to a stirred solution of the compound [7a] (1.00 g) in methanol (50 mL) at room temperature. The mixture was stirred at 40–50° C. for 3–4 hours (TLC monitoring) and evaporated under reduced pressure. The residue was diluted with dichloromethane (75 mL). The solution was washed with saturated aqueous solution of sodium bicarbonate (25 mL) and brine (25 mL), dried over sodium sulfate, filtered and evaporated to give 0.69 g (81.0%) of oily residue. The residue was crystallized from a mixture of ethyl acetate and isopropyl ether to give compound [5a] as white crystals with mp 126–128° C. $^1$H NMR (CDCl$_3$) is in agreement with the structure.

4) Regeneration of (3aR,4R,5R,6aS)-hexahydro-4-(3-oxo-5-phenyl-1E-pentenyl)-5-(p-phenyl-benzoyloxy)-2H-cyclopenta[b]furan-2-one [4a]

4.1) From Compound [6a]

A solution of pyridine sulfur trioxide (0.32 g) in DMSO (3.5 mL) was added dropwise to a stirred solution of compound [6a] (0.30 g) and triethylamine (0.40 g) in dichloromethane (4 mL) at –5–0° C. The mixture was stirred at the same temperature for 1 hour (TLC monitoring) and poured into cold water (15 mL). The mixture was stirred for 10 min at 0–5° C. The organic layer was separated, the water layer was extracted with dichloromethane (3×5 mL). The combined organic layers were washed with brine (3×10 mL), dried over sodium sulfate, filtered and evaporated under reduced pressure. A solution of the residue in methanol (1 mL) was cold to –10° C. and kept at the same temperature for 3 hours. The precipitated crystals were filtered, washed on filter with cold methanol (2×1 mL) and dried under reduced pressure to a constant weight to give 0.26 g (87% yield) of crystalline compound [4a] with 94% purity by HPLC.

4.2) From Compound [5a]

A solution of pyridine sulfur trioxide (0.60 g) in DMSO (7.0 mL) was added dropwise to a stirred solution of compound [5a] (0.60 g) and triethylamine (0.80 g) in dichloromethane (8 mL) at –5–0° C. The mixture was stirred at the same temperature for 1 hour (TLC monitoring) and poured into cold water (30 mL). The mixture was stirred for 10 min at 0–5° C. The organic layer was separated, the water layer was extracted with dichloromethane (3×10 mL). The combined organic layers were washed with brine (3×20 mL), dried over sodium sulfate, filtered and evaporated under reduced pressure. A solution of the residue in methanol (2 mL) was cold to –10° C. and kept at the same temperature for 3 hours. The precipitated crystals were filtered, washed on filter with cold methanol (2×2 mL) and dried under reduced pressure to a constant weight to give 0.50 g (83.7% yield) of crystalline compound [4a].

EXAMPLE 3

(3aR,4R,5R,6aS)-Hexahydro-5-(p-phenylbenzoyloxy)-4-[(3R)-5-phenyl-3-[(tetrahydro-2H-pyran-2-yl)oxy]pentyl]-2H-cyclopenta[b]furan-2-one [9a]

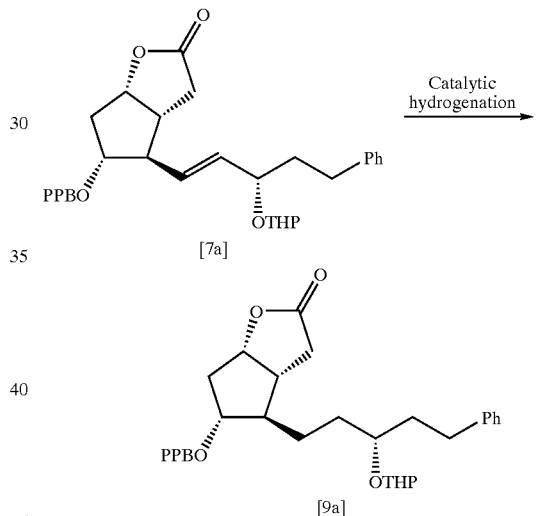

wherein PPB is p-phenylbenzoyl group and THP is tetrahydro-2H-pyran-2-yl group.

A mixture of a compound [7a] (80.0 g), palladium on carbon catalyst (16 g) and ethyl acetate (1.0 L) was stirred under hydrogen atmosphere at 150 psi for 3 hours at room temperature. The reaction mixture was then filtered and evaporated under reduced pressure. The oily residue was crystallized from a mixture of hexane and ethyl acetate 4:1 v/v to give 71.4 g (89% yield) of compound [9a], mp 103–105° C., $[\alpha]_D^{20}$ –107° (c 1.0, MeCN). $^1$H NMR (CDCl$_3$) δ: 8.03 (d, J=8 Hz, 2H); 7.60–7.67 (m, 4H); 7.36–7.48 (m, 3H); 7.14–7.24 (m, 5H); 5.20–5.30 (m, 1H); 5.00–5.15 (m, 1H); 4.50–4.70 (m, 1H), 3.89–3.95 (m, 1H); 3.66–3.72 (m, 1H); 3.45–3.50 (m, 1H). $^{13}$C NMR (CDCl$_3$) δ: 20.1; 25.4; 28.7; 31.3; 31.9; 36.5; 43.5; 52.8; 63.0; 76.0; 80.1; 84.3; 97.8; 125.7; 127.1; 127.2; 128.1; 128.3; 128.4; 128.9; 130.1; 140.0; 142.4; 146.0; 165.8; 176.7. IR (KBr): 2990; 1771; 1707; 1608; 1277; 1181; 1110; 1026; 751; 698 cm$^{-1}$.

EXAMPLE 4

(3aR,4R,5R,6aS)-3-Hexahydro-5-(p-phenylbenzoyloxy)-4-[(3S-5-phenyl-3-[(tetrahydro-2H-pyran-2-yl)oxy]pentyl]-2H-cyclopenta[b]furan-2-one [22]

Scheme 11

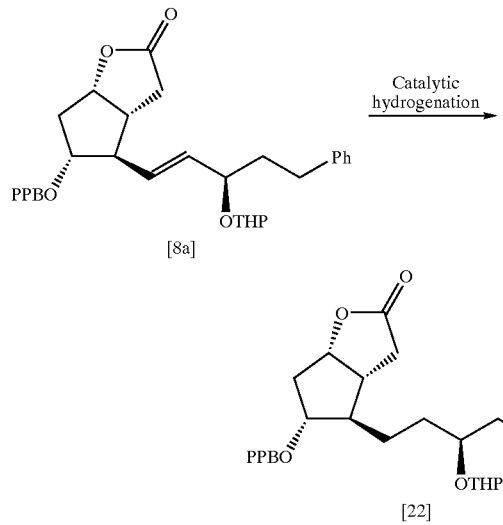

wherein PPB is p-phenylbenzoyl group and THP is tetrahydro-2H-pyran-2-yl group.

A mixture of a compound [8a] (1.4 g), palladium on carbon catalyst (0.56 g) and ethyl acetate (40 mL) was stirred under hydrogen atmosphere at 40 psi for 3 hours at room temperature. The reaction mixture was then filtered and evaporated under reduced pressure. The oily residue was purified by column chromatography on silica gel elution with mixture of hexane and ethyl acetate 2:1 v/v to give 1.2 g (86% yield) of compound [22] as oil, $[\alpha]_D^{20}$ −52.30 (c 1.0, MeCN). $^1$H NMR (CDCl$_3$) δ: 1.41–1.86 (m, 12H); 2.00–2.25 (m, 1H); 2.34–3.00 (m, 7H); 3.40–3.60 (m, 1H); 3.60–3.80 (m, 1H); 3.80–4.00 (m, 1H); 5.00–5.15 (m, 1H); 4.50–4.70 (m, 1H); 3.89–3.95 (m, 1H); 3.66–3.72 (m, 1H); 3.45–3.50 (m, 1H).

EXAMPLE 5

(3aR,4R,5R,6aS)-Hexahydro-5-(p-phenylbenzoyloxy)-4-[(3R)-5-phenyl-3-[(tetrahydro-2H-pyran-2-yl)oxy]pentyl]-2H-cyclopenta[b]furan-2-one [9a]

Scheme 12

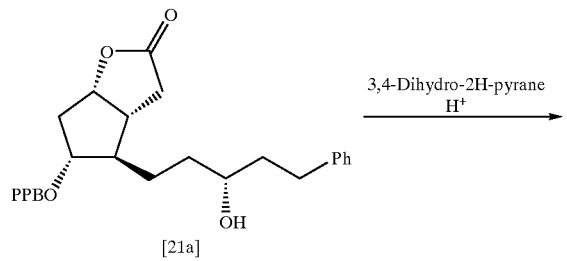

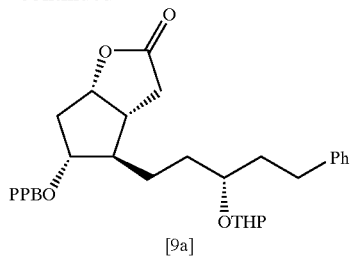

wherein PPB is p-phenylbenzoyl group and THP is tetrahydro-2H-pyran-2-yl group.

Pyridinium p-toluenesulfonate (20 mg) was added to a stirred solution of compound [21a] (2.4 g) and 3,4-Dihydro-2H-pyran (1.6 g) in dichloromethane (25 mL) at room temperature. The mixture was stirred overnight at room temperature (TLC monitoring), washed with saturated aqueous solution of sodium bicarbonate and brine, dried over sodium sulfate, filtered and evaporated under reduced pressure. The residue was crystallized from ether and recrystallized from mixture of hexane and ethyl acetate to give 2.31 g (82% yield) the compound [9a], mp 103–105° C. $^1$H NMR (CDCl$_3$) agrees with the structure

EXAMPLE 6

(3aR,4R,5R,6aS)-Hexahydro-5-(p-phenylbenzoyloxy)-4-[(3R)-5-phenyl-3-[(tetrahydro-2H-pyran-2-yl)oxy]pentyl]-2H-cyclopenta[b]furan-2-ol [10a]

Scheme 13

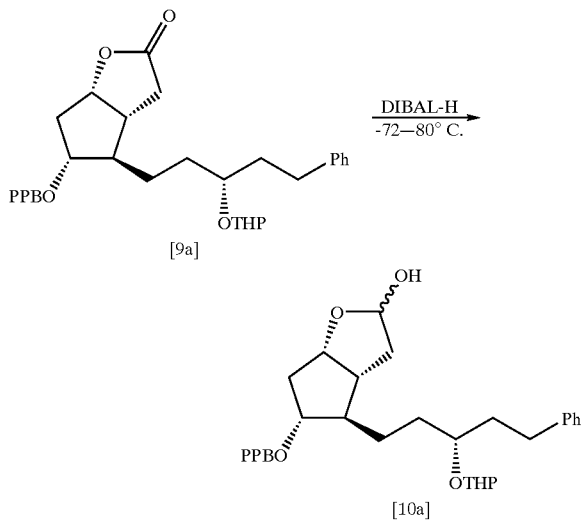

wherein PPB is p-phenylbenzoyl group and THP is tetrahydro-2H-pyran-2-yl group.

A 1.5 M solution of diisobutylaluminum hydride in toluene (6.0 mL, 9.0 mmol) was added dropwise to a stirred solution of compound [9a] (4.1 g, 7.2 mmol) in toluene (60 mL) at −70–−80° C. (acetone/dry ice bath) and the resulting mixture was stirred during 1 h at the same temperature. Methanol (10 mL) was added dropwise to the stirred mixture at −70–−80° C. The mixture was stirred for 1 hour at room temperature, filtered and evaporated under reduced pressure. Dichloromethane (30 mL) was added to the residue. The resulting solution was washed with brine (2×10 mL), dried over sodium sulfate, filtered and evaporated under reduced pressure. The residue was purified by column chromatography on silica gel (hexane/ethyl acetate 2:1 v/v) to obtain 2.0 g (49% yield) of the compound [10a]. $^1$H NMR (CDCl$_3$) δ: 6.4–6.5 (m, 1H); 5.0–5.2 (m, 1H); 4.7–4.9 (m, 1H); 4.5–4.7 (m, 1H); 3.8–4.0 (m, 1H); 3.6–3.8 (m, 1H); 3.4–3.6 (m, 1H). $^{13}$C NMR (CDCl$_3$) δ: 20.1; 25.5; 28.6; 31.3; 31.6; 36.7; 37.7; 40.3; 41.1; 46.2; 51.6; 63.0; 81.3; 82.0; 97.8; 100.2; 125.6; 127.1; 127.2; 128.1; 128.3; 128.4; 128.9; 129.2; 130.0; 130.1; 140.0; 145.7; 166.0. IR (KBr): 3500, 2945, 1712, 1605, 1278, 1117, 1026, 752 cm$^{-1}$.

EXAMPLE 7

(3a,4R,5R,6aS)-Hexahydro-5-hydroxy-4-[(3R)-5-phenyl-3-[(tetrahydro-2H-pyran-2-yl)oxy]pentyl]-2H-cyclopenta[b]furan-2-ol [11a]

Scheme 14

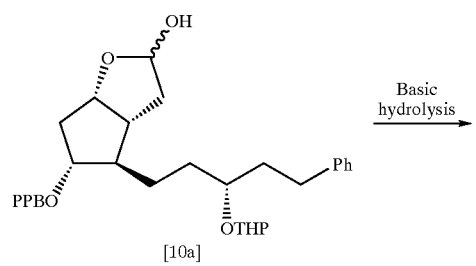

[10a]

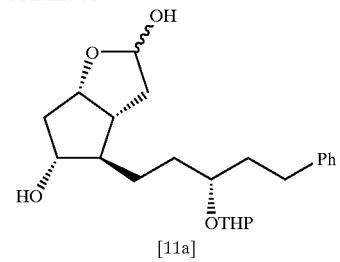

[11a]

wherein PPB is p-phenylbenzoyl group and THP is tetrahydro-2H-pyran-2-yl group.

A mixture of compound [10a] (2.0 g) and potassium carbonate (1.0 g) in methanol (10 mL) was stirred at 40–45° C. for 5 hours (TLC monitoring). Dichloromethane (20 mL) and water (20 mL) were added to the stirred mixture at room temperature. Organic layer was separated, washed with water, dried over sodium sulfate, filtered and evaporated under reduced pressure. The residue was purified by column chromatography on silica gel. The compound [11a] (1.0 g, 73% yield) was prepared.

EXAMPLE 8

(3aR,4R,5R,6aS)-Hexahydro-5-hydroxy-4-[(3R)-5-phenyl-3-[(tetrahydro-2H-pyran-2-yl)oxy]pentyl]-2H-cyclopenta[b]furan-2-ol [11a]

Scheme 15

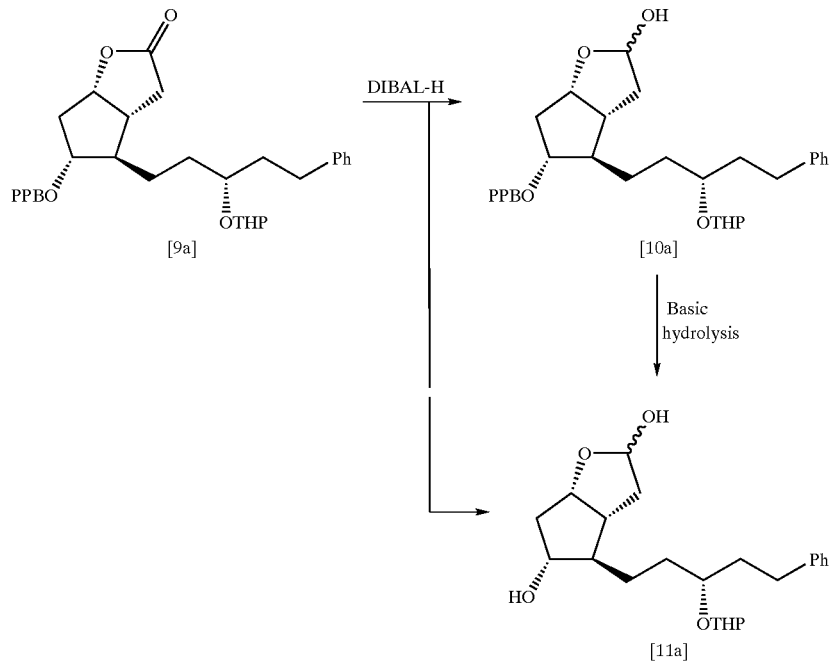

wherein PPB is p-phenylbenzoyl group and THP is tetrahydro-2H-pyran-2-yl group.

A 1.5 M solution of Diisobutylaluminum hydride in toluene (46.0 g, 69 mmol) was added dropwise to a stirred solution of compound [9a] (17.0 g, 30 mmol) in toluene (500 mL) at −20—−10° C. The mixture was stirred for 1 hour at the same temperature. Methanol (200 mL) was added dropwise to the stirred mixture at −20—−10° C. The obtained mixture was stirred for 1 hour at room temperature, filtered and evaporated under reduced pressure. Dichloromethane (250 mL) was added to the residue. The resulting solution was washed with brine (2×220 mL), dried over sodium sulfate, filtered and evaporated under reduced pressure. To complete hydrolysis of p-phenylbenzoate-groups a mixture of the residue and potassium carbonate (10:0 g) in methanol (100 mL) was stirred at room temperature for 7 hours (TLC monitoring). The mixture was evaporated under reduced pressure. A mixture of the residue, dichloromethane (300 mL) and water (300 mL) was stirred for 10 min at room temperature. The organic layer was separated, washed with brine, dried over sodium sulfate, filtered and evaporated under reduced pressure. The residue was purified by column chromatography on silica gel exane/ethyl acetate 1:2 v/v) to obtain 10.3 g of the compound [11a] (88% yield), $[\alpha]_D^{20}$ −53.5° (c 1.0, MeCN). $^1$H NMR (CDCl$_3$) δ: 7.10–7.29 (m, 5H); 5.47–5.63 (m, 1H); 4.57–4.69 (m, 2H); 3.69–3.94 (m, 2H); 3.60–3.75 (m, 1H); 3.40–3.55 (m, 1H). $^{13}$C NMR (CDCl$_3$) δ: 19.9; 25.4; 29.0; 31.2; 31.9; 36.6; 40.2; 41.5; 42.5; 46.4; 48.0; 55.3; 55.6; 62.8; 79.4; 79.9; 82.4; 86.4; 97.6; 100.0; 101.1; 125.6; 128.2; 128.3; 142.5. IR (neat): 3398, 2944, 2867, 1451 cm$^{-1}$.

EXAMPLE 9

(3aR,4R,5R,6aS)-Hexahydro-5-hydroxy-4-[(3R)-5-phenyl-3-[(tetrahydro-2H-pyran-2-yl)oxy]pentyl]-2H-cyclopenta[b]furan-2-ol [11a]

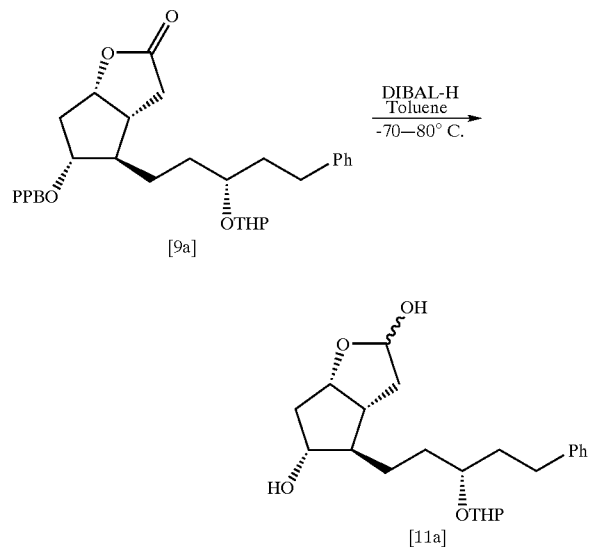

wherein PPB is p-phenylbenzoyl group and THP is tetrahydro-2H-pyran-2-yl group.

A 1.5 M solution of Diisobutylaluminum hydride in toluene (12.6 mL, 18.9 mmol) was added dropwise to a stirred solution of a compound [9a] (4.1 g, 7.2 mmol) in toluene (60 mL) at −70—−80° C. (acetone/dry ice bath). The mixture was stirred for 1 hour at the same temperature. Methanol (50 mL) was added dropwise to the stirred mixture at −70—−80° C. and the cooling bath was removed. The mixture was stirred for 1 hours at room temperature, filtered and evaporated under reduced pressure. A solution of the residue in dichloromethane (150 mL) was washed with brine (2×10 mL), dried over sodium sulfate, filtered and evaporated under reduced pressure. The residue was purified by column chromatography on silica gel (hexane/ethyl acetate 1:2 v/v) to obtain compound [11a] (2.53 g, 90% yield).

EXAMPLE 10

(1R,2R,3R,5S)-3,5-dihydroxy-2-[(3R)-5-phenyl-3-[(tetrahydro-2H-pyran-2-yl)oxy]pentyl]cyclopentaneethanol [12a]

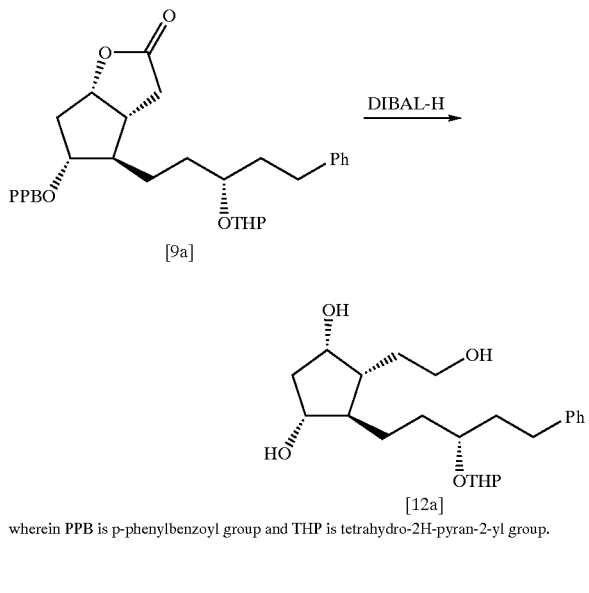

wherein PPB is p-phenylbenzoyl group and THP is tetrahydro-2H-pyran-2-yl group.

A 1.5 M solution of diisobutylaluminum hydride in toluene (12.6 mL, 18.9 mmol) was added dropwise to a stirred solution of a compound [9a] (2.0 g, 3.5 mmol) in toluene (60 mL) at room temperature. The mixture was stirred for 3 hour at the same temperature. Methanol (50 mL) was added dropwise to the stirred mixture at −5—+5° C. and the cooling bath was removed. The mixture was stirred for 1 hours at room temperature, filtered and evaporated under reduced pressure. The residue was purified by column chromatography on silica gel (hexane/ethyl acetate 1:5 v/v) to obtain 1.0 g (73% yield) of the compound [12a]. $^1$H and $^{13}$C NMR are in agreement with the structure.

EXAMPLE 11

(3aR,4R,5R,6aS)-Hexahydro-5-hydroxy-4-[(3R)-5-phenyl-3-hydroxypentyl]-2H-cyclopenta[b]furan-2-ol [11b]

Scheme 18

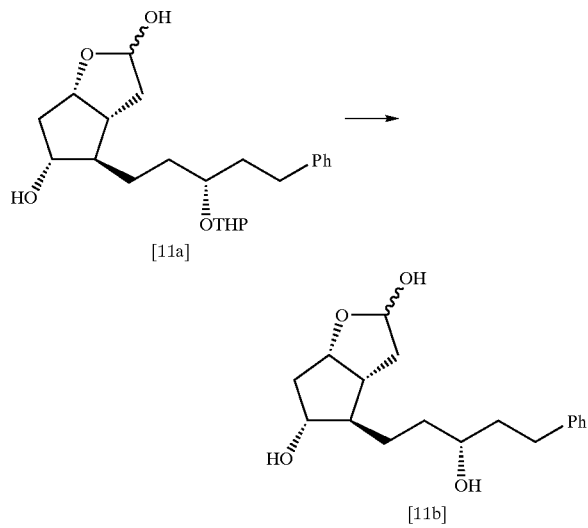

wherein THP is tetrahydro-2H-pyran-2-yl group.

A mixture of compound [11a] (0.55 g), acetic acid (2 ml), THF (2 mL) and water (2 mL) was stirred at 40–50° C. for 4 hours (TLC monitoring). The mixture was basified with 1 N aq. potassium hydroxide to pH 10–11 and the product was extracted with dichloromethane (3×20 mL). The combined organic layers were dried over sodium sulfate, filtered and evaporated under reduced pressure. The residue was purified by column chromatography on silica gel (elution with gradient ethyl acetate/hexane from 1:2 to 3:1 v/v) to give 0.18 g (43%) of the compound [11b] as a colorless oil. $^1$H NMR (CD$_3$OD) is compatible with literature data.

EXAMPLE 12

7-[(1R,2R,3R,5S)-3,5-dihydroxy-2-[(3R)-5-phenyl-3-[(tetrahydro-2H-pyran-2-yl)oxy]pentyl]cyclopentyl]-5Z-heptenoic acid [13a]

Scheme 19

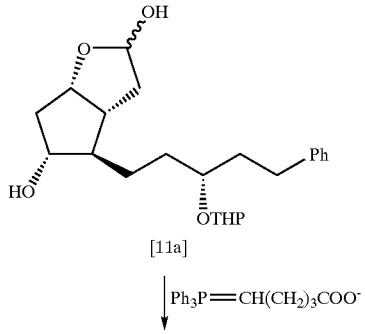

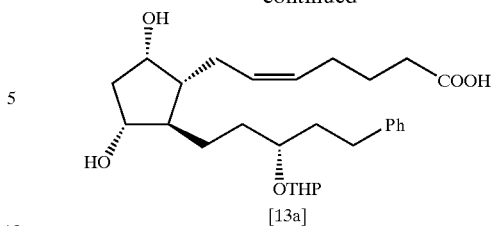

wherein PPB is p-phenylbenzoyl group and THP is tetrahydro-2H-pyran-2-yl group.

Potassium tert-butoxide (33.3 g) was added to a stirred suspension of (4-carboxybutyl)triphenylphosphonium bromide (66.0 g) in THF (200 mL) at 0–5° C. and the mixture was stirred at room temperature during 0.5 h. A solution of compound [11a] (13.0 g) in THF (100 mL) was added dropwise during 2 hours to the resultant red orange suspension of potassium 5-(triphenylphosphoranylidene)pentanoate at −15° C. The mixture was stirred for 3 hours at this temperature (TLC monitoring) and poured into ice water (1 L). The alkaline solution was washed with t-BuOMe (4×500 mL), mixed with ether (500 mL) and acidified with 10% aqueous solution of citric acid to pH 4. The white precipitated crystals were filtered off and washed on filter with ether (200 mL). The ether layer was separated from combined filtrates. The water phase was extracted with ether (200 mL). The combined organic extracts were concentrated to a volume 400 mL, washed with water (5×200 mL), dried over sodium sulfate, filtered and evaporated under reduced pressure to give 13.5 g (86% yield) of the compound [13a].

EXAMPLE 13

Latanoprost Acid [13b]

Scheme 20

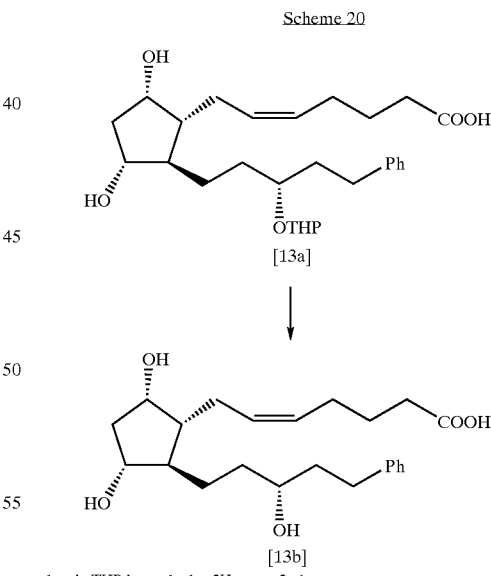

wherein THP is tetrahydro-2H-pyran-2-yl group.

Pyridinium p-toluenesulfonate (70 mg) was added to a stirred solution of the compound [13a] (1.8 g) in methanol (50 mL) at room temperature. The mixture was stirred at 50° C. over a period of 4 h, by which time the reaction was complete (HPLC monitoring). The mixture was evaporated under reduced pressure. Water (10 mL) and ethanol (10 mL) were added to a residue. The mixture was basified with 1 N aq. NaOH to pH 12, stirred for 1 hour at 70–75° C. and evaporated under reduced pressure. A solution of the residue in water (50 mL) was extracted with ethyl acetate (5×20 mL), acidified with 10% aq. citric acid to pH 4 and extracted with ether (3×50 mL). The combined organic extracts were dried over sodium sulfate, filtered and evaporated under reduced pressure to give 1.35 g (96% yield) of compound [13b] as colorless oil. The compound [13b] may be purified by chromatography on silica gel (elution with hexane/ethyl acetate 1:1 v/v) or by crystallization its salts with tromethamine, histamine, L-arginine, triptamine or adamantanamine from various solvents following isolation of the purified compound [13b] from the salts.

EXAMPLE 14

7-[(1R,2R,3R,5S)-3,5-dihydroxy-2-[(3R)-5-phenyl-3-[(tetrahydro-2H-pyran-2-yl)oxy]pentyl] cyclopentyl]-5Z-heptenoic acid, isopropyl ester [17a]

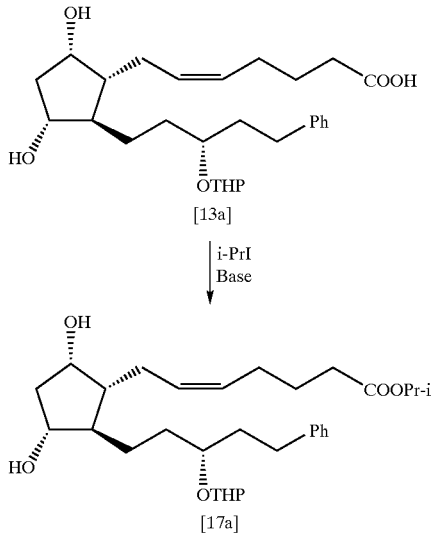

wherein THP is tetrahydro-2H-pyran-2-yl group.

1,8-Diazabicyclo[5.4.0]undec-7-ene (3.73 g) was added dropwise to a stirred solution of compound [13a] (1.66 g) in acetone (15 mL) at 0° C. The solution was warmed to room temperature, and isopropyl iodide (3.6 g) was added dropwise to it. The resulting mixture was stirred overnight at room temperature (TLC monitoring). The mixture was concentrated to a volume 5 mL, dichloromethane (70 mL) was added and the resulting mixture was washed with 3% aqueous solution of citric acid (2×20 mL), 5% aqueous solution of sodium bicarbonate (2×10 mL) and brine, dried over sodium sulfate, filtered and evaporated under reduced pressure. The residue (1.8 g) was purified by column chromatography on silica gel (eluent hexane/ethyl acetate 2:1 v/v) to obtain 1.3 g (72% yield) of the compound [17a]. $^1$H NMR (CDCl$_3$) δ: 7.14–7.29 (m, 5H); 5.27–5.46 (m, 2H); 4.91–5.03 (mn, 1H); 4.58–4.64 (m, 1H); 4.07–4.13 (m, 1H); 3.71–3.92 (m, 2H); 3.66–3.71 (m, 1H); 3.45–3.50 (m, 1H); 1.19 (d, J=8 Hz, 6H). $^{13}$C NMR (CDCl$_3$) δ: 20.0; 20.4; 21.8; 25.0; 25.5; 26.7; 27.1; 29.1; 31.3; 32.0; 34.1; 36.7; 42.5; 51.8; 53.3; 62.9; 67.5; 74.8; 78.9; 97.8; 125.6; 125.8; 128.3; 128.4; 129.3; 129.5; 129.6; 143.0; 173.3.

EXAMPLE 15

Latanoprost [1]

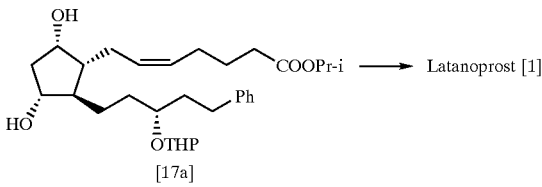

wherein THP is tetrahydro-2H-pyran-2-yl group.

Pyridinium p-toluenesulfonate (16 mg) was added to a stirred solution of the compound [17a] (0.7 g) in ethanol (20 mL) at room temperature. The mixture was stirred at 50° C. over a period of 3 hours, by which time the reaction was complete (TLC monitoring). The mixture was concentrated under reduced pressure. The residue was diluted with dichloromethane (40 mL). The solution was washed with water (10 mL) and brine (10 mL), dried over sodium sulfate and evaporated under reduced pressure. The residue was purified by column chromatography on silica gel (hexane/ethyl acetate 1:1 v/v) to obtain Latanoprost. $^1$H NMR (CDCl$_3$) is compatible with literature data.

EXAMPLE 16

Latanoprost [1]

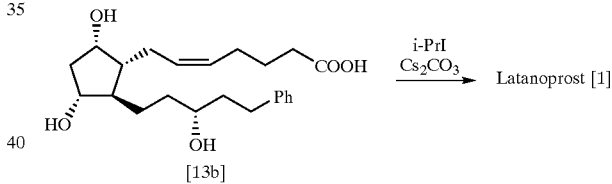

A mixture of Latanoprost acid [13b] (0.95 g, 2.4 mmol), isopropyl iodide (0.83 g, 4.8 mmol), cesium carbonate (1.20 g, 3.6 mmol) and DMF (20 mL) was stirred for 2–3 hours at 40–50° C. (TMC monitoring) and poured into a stirred mixture of 2 M aqueous NaHSO$_4$ (2.5 mL, 5 mmol), ice (50 mL) and ether (50 mL). The organic layer was separated and the water phase was extracted with ether (2×50 mL). The combined organic layers were washed with brine (50 mL), dried over sodium sulfate, filtered and evaporated under reduced pressure to give 1.05 g (100% yield) of crude product. The crude product was purified by column chromatography on silica gel (hexane/ethyl acetate 1:1 v/v) to give Latanoprost. $^1$H NMR (CDCl$_3$) is compatible with literature data.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A process for the preparation of Latanoprost [1]

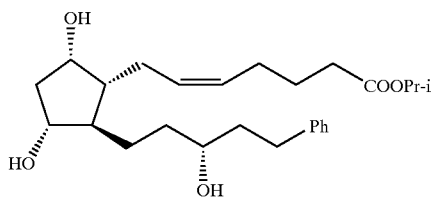
[1]

which comprises deriving the compound [5]

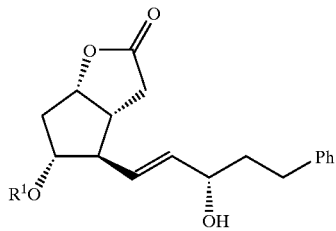
[5]

to give the compound [7]

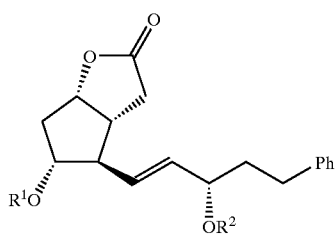
[7]

which is hydrogenated in the presence of catalyst to give the compound of the Formula [9]

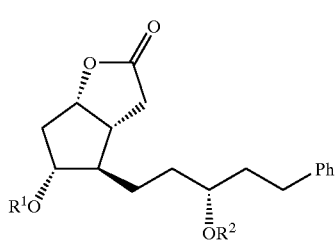
[9]

which is reduced with diisobutylaluminum hydride at temperature range from −50 to +50° C. followed by hydrolysis of the obtained reaction mixture under basic conditions to give compound [11], which is converted into latanoprost [1]

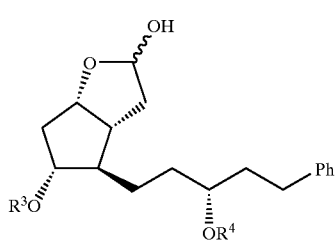
[11]

wherein one of $R^1$ and $R^2$ is an aryl carbonyl and the other one is selected from the group consisting of aryl carbonyl, acyl, trialkylsilyl, dialkylarylsilyl, 1-alkoxyalkyl, unsubstituted and alkyl-substituted tetrahydro-2H-pyran-2-yl and tetrahydrofuran-2-yl groups, and $R^3$ is hydrogen when $R^1$ is acyl and is equal to $R^1$ when it is trialkylsilyl, dialkylarylsilyl, 1-alkoxyalkyl, unsubstituted or alkyl-substituted tetrahydro-2H-pyran-2-yl or tetrahydrofuran-2-yl groups; $R^4$ is hydrogen when $R^2$ is acyl and is equal to $R^2$ when it is trialkylsilyl, dialkylarylsilyl, 1-alkoxyalkyl, unsubstituted or alkyl-substituted tetrahydro-2H-pyran-2-yl or tetrahydrofuran-2-yl groups.

2. A process according to claim 1 wherein the said reduction of the compound [9] with diisobutylaluminum hydride is provided at temperature range from −20 to +20° C.

3. A process according to claim 1 wherein the said catalyst contains palladium, platinum or nickel.

4. A process according to claim 1 wherein the said catalyst is palladium on carbon.

5. A process according to claim 1 wherein the said hydrogenation of the compound [7] is carried out in the presence of bases and/or salts.

6. The process defined in claim 1, which comprises isolating the compounds of Formulae [7] and [9] in the course of the synthesis and, if desired, purifying them by re-crystallization.

7. Compound of the formula [7]:

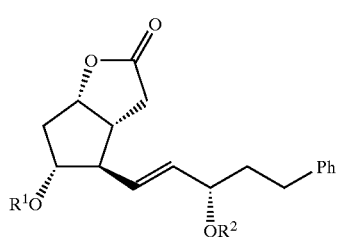
[7]

wherein one of $R^1$ and $R^2$ is p-phenylbenzoyl group and the other one is selected from the group consisting of aryl carbonyl, acyl, trialkylsilyl, dialkylarylsilyl, 1-alkoxyalkyl, unsubstituted and alkyl-substituted tetrahydro-2H-pyran-2-yl and tetrahydrofuran-2-yl groups.

8. Compound of the formula [9]:

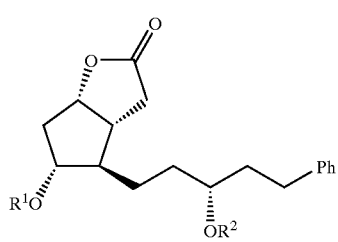
[9]

wherein one of $R^1$ and $R^2$ is an aryl carbonyl group and the other one is selected from the group consisting of aryl carbonyl, acyl, trialkylsilyl, dialkylarylsilyl, 1-alkoxyalkyl, unsubstituted and alkyl-substituted tetrahydro-2H-pyran-2-yl and tetrahydrofuran-2-yl groups.

9. Compound of the formula [11]:

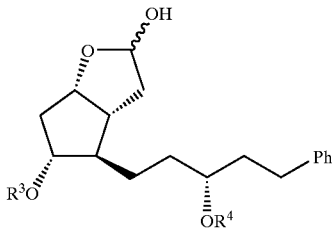

[11]

wherein $R^3$ and $R^4$ are selected from the group consisting of hydrogen, trialkylsilyl, dialkylarylsilyl, 1-alkoxyalkyl, unsubstituted and alkyl-substituted tetrahydro-2H-pyran-2-yl and tetrahydrofuran-2-yl groups, and one of the $R^3$ and $R^4$ is hydrogen group.

10. (3aR,4R,5R,6aS)-Hexahydro-5-(p-phenylbenzoyloxy)-4-[(3S)-5-phenyl-3-[(tetrahydro-2H-pyran-2-yl)oxy]-1E-pentenyl]-2H-cyclopenta[b]furan-2-one [7a]:

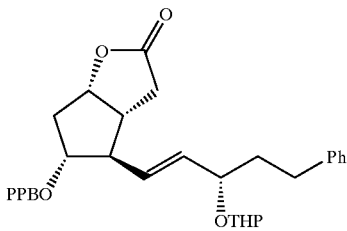

[7a]

wherein PPB is p-phenylbenzoyl group and THP is tetrahydro-2H-pyran-2-yl group.

11. (3aR,4R,5R,6aS)-Hexahydro-5-(p-phenylbenzoyloxy)-4-[(3R)-5-phenyl-3-[(tetrahydro-2H-pyran-2-yl)oxy]pentyl]-2H-cyclopenta[b]furan-2-one [9a]:

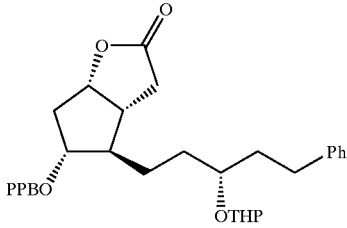

[9a]

wherein PPB is p-phenylbenzoyl group and THP is tetrahydro-2H-pyran-2-yl group.

12. (3aR,4R,5R,6aS)-Hexahydro-5-hydroxy-4-[(3R)-5-phenyl-3-[(tetrahydro-2H-pyran-2-yl)oxy]pentyl]-2H-cyclopenta[b]furan-2-ol [11a]:

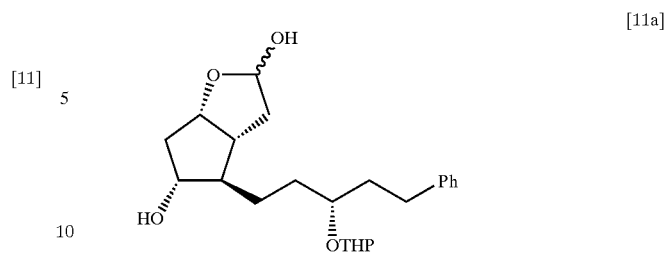

[11a]

wherein THP is tetrahydro-2H-pyran-2-yl group.

13. A process according to claim 1 wherein $R^1$ and $R^2$ are selected from the group consisting of benzoyl, p-toluoyl, p-phenylbenzoyl and tetrahydro-2H-pyran-2-yl groups, and at least one of the $R^1$ and $R^2$ is arylcarbonyl group.

14. A process according to claim 1, wherein compound [11] is converted into latanoprost [1] by reacting [11] with a metal salt of 5-(triphenylphosphoranylidene)pentanoic acid to form a compound of formula [13]

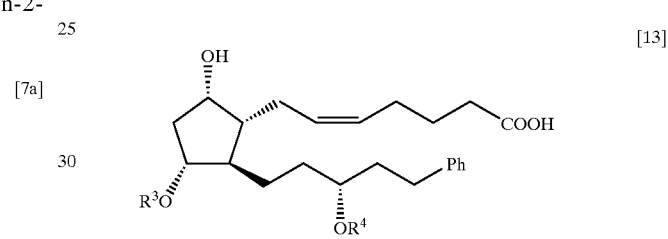

[13]

wherein $R^3$ and $R^4$ are as defined above;

and when $R^3$ and/or $R^4$ in compound [13] is other than hydrogen, removing the protecting group to yield latanoprost acid [13b]

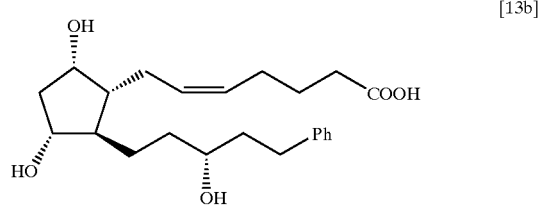

[13b]

following esterifycation of compound [13b] with compound [16]:

(CH$_3$)$_2$CHX  [16]

wherein X is a leaving group, in the presence of a base to obtain latanoprost [1].

15. A process according to claim 14, wherein said base is cesium carbonate.

* * * * *